(12) United States Patent
Fujii et al.

(10) Patent No.: US 11,446,520 B2
(45) Date of Patent: Sep. 20, 2022

(54) RADIATION THERAPY APPARATUS CONFIGURED TO TRACK A TRACKING OBJECT MOVING IN AN IRRADIATION OBJECT

(71) Applicant: National University Corporation Hokkaido University, Sapporo (JP)

(72) Inventors: Takaaki Fujii, Sapporo (JP); Seishin Takao, Sapporo (JP); Naoki Miyamoto, Sapporo (JP); Taeko Matsuura, Sapporo (JP); Kikuo Umegaki, Sapporo (JP)

(73) Assignee: National Univ. Corporation Hokkaido Univ., Hokkaido (JP)

( * ) Notice: Subject to any disclaimer, the term of this patent is extended or adjusted under 35 U.S.C. 154(b) by 11 days.

(21) Appl. No.: 16/493,955

(22) PCT Filed: Mar. 12, 2018

(86) PCT No.: PCT/JP2018/009499
§ 371 (c)(1),
(2) Date: Sep. 13, 2019

(87) PCT Pub. No.: WO2018/168766
PCT Pub. Date: Sep. 20, 2018

(65) Prior Publication Data
US 2020/0009404 A1 Jan. 9, 2020

(30) Foreign Application Priority Data
Mar. 14, 2017 (JP) .............................. JP2017-047982

(51) Int. Cl.
*A61N 5/10* (2006.01)
*A61B 90/00* (2016.01)

(52) U.S. Cl.
CPC ............ *A61N 5/1049* (2013.01); *A61B 90/39* (2016.02); *A61N 5/1037* (2013.01);
(Continued)

(58) Field of Classification Search
CPC ...... A61N 5/10; A61N 5/1037; A61N 5/1048; A61N 5/1049; A61N 2005/1061;
(Continued)

(56) References Cited

U.S. PATENT DOCUMENTS 6,842,502 B2 * 1/2005 Jaffray .................. A61B 6/466
378/65
6,888,919 B2 * 5/2005 Graf ..................... A61N 5/1049
378/197

(Continued)

FOREIGN PATENT DOCUMENTS

JP 2010-005427 A 1/2010
JP WO 2008/102843 A1 5/2010

(Continued)

OTHER PUBLICATIONS

International Search Report for Application No. PCT/JP2018/009499, dated May 22, 2018, with English translation (5 pages).
(Continued)

*Primary Examiner* — Allen C. Ho
(74) *Attorney, Agent, or Firm* — Nixon Peabody LLP

(57) ABSTRACT

Through the present invention, three-dimensional coordinates of a tracking object moving in an irradiation object can be calculated from fluoroscopic X-ray images captured and acquired from various angles in a single fluoroscopic X-ray device mounted to a radiation therapy apparatus. The three-dimensional coordinates of the tracking object are calculated on a straight tracking object presence line connecting an X-ray generating device for fluoroscopy and the position in an X-ray plane detector of the tracking object on the
(Continued)

fluoroscopic X-ray image acquired by the X-ray generating device for fluoroscopy and the X-ray plane detector, and using line segment information included in a movement region of the tracking object set in advance.

7 Claims, 15 Drawing Sheets

(52) U.S. Cl.
CPC ......... *A61N 5/1048* (2013.01); *A61N 5/1064* (2013.01); *A61N 5/1071* (2013.01); *A61N 2005/1061* (2013.01)

(58) Field of Classification Search
CPC .. A61N 5/1064; A61N 5/1065; A61N 5/1067; A61N 5/1068; A61N 5/1069; A61N 5/107; A61N 5/1071
USPC .......................................................... 378/65
See application file for complete search history.

(56) References Cited

U.S. PATENT DOCUMENTS

| | | | | |
|---|---|---|---|---|
| 7,469,035 B2* | 12/2008 | Keall | ................... | A61N 5/1042 378/205 |
| 7,978,817 B2* | 7/2011 | Rietzel | ................. | A61N 5/1049 378/65 |
| 8,086,004 B2* | 12/2011 | Kuduvalli | ............ | A61N 5/1075 382/128 |
| 8,090,074 B2* | 1/2012 | Filiberti | ................. | G16H 20/40 378/65 |
| 8,130,907 B2* | 3/2012 | Maurer, Jr. | .............. | A61B 6/12 378/65 |
| 8,229,068 B2* | 7/2012 | Lu | ........................ | A61N 5/1049 378/65 |
| 8,428,218 B2* | 4/2013 | Kaneko | ................ | A61N 5/1049 378/65 |
| 8,428,219 B2* | 4/2013 | Friedrich | ............... | A61B 6/032 378/65 |
| 8,767,917 B2* | 7/2014 | Ruchala | ................. | A61N 5/103 378/65 |
| 8,824,630 B2* | 9/2014 | Maurer, Jr. | .......... | A61N 5/1067 378/65 |
| 8,849,633 B2* | 9/2014 | Core | .................... | A61B 6/5264 703/6 |
| 9,489,734 B2* | 11/2016 | Gum | .................... | A61N 5/1049 |
| 9,616,249 B2* | 4/2017 | Miyamoto | ............. | A61B 6/487 |
| 9,724,049 B2* | 8/2017 | Umekawa | ............ | A61B 6/5294 |
| 9,911,199 B2* | 3/2018 | Vilsmeier | ............ | A61B 6/5217 |
| 9,968,321 B2* | 5/2018 | Wikler | ................... | A61B 6/488 |
| 10,201,717 B2* | 2/2019 | Berlinger | ............. | A61N 5/1049 |
| 10,315,049 B2* | 6/2019 | Gauthier | ............. | A61N 5/1039 |
| 10,426,554 B2* | 10/2019 | Siewerdsen | ............ | A61B 34/20 |
| 10,631,778 B2* | 4/2020 | Kleiner | ................ | A61N 5/1068 |
| 10,776,959 B2* | 9/2020 | Berlinger | ............... | A61B 6/486 |
| 2002/0193685 A1 | 12/2002 | Mate | | |
| 2010/0142677 A1 | 6/2010 | Kaneko | | |
| 2015/0036793 A1 | 2/2015 | Umekawa | | |
| 2015/0087881 A1 | 3/2015 | Miyamoto | | |
| 2016/0174921 A1 | 6/2016 | Wiler | | |

FOREIGN PATENT DOCUMENTS

| | | |
|---|---|---|
| JP | 2013-192702 A | 9/2013 |
| JP | 2015-029793 A | 2/2015 |
| JP | 2016-120282 A | 7/2016 |
| WO | WO 2004/066211 A1 | 8/2004 |

OTHER PUBLICATIONS

Written Opinion of International Searching Authority for Application No. PCT/JP2018/009499, dated May 22, 2018, English translation unavailable (4 pages).

\* cited by examiner

RADIATION THERAPY APPARATUS CONFIGURED TO TRACK A TRACKING OBJECT MOVING IN AN IRRADIATION OBJECT

CROSS-REFERENCE TO RELATED APPLICATIONS

This application is a U.S. National Stage of International Application No. PCT/JP2018/009499, filed Mar. 12, 2018, which is related to and claims the benefit and priority of Japanese Patent Application No. 2017-047982, filed Mar. 14, 2017, the contents of which are incorporated herein in their entireties by reference.

TECHNICAL FIELD

The present invention relates to a radiation therapy apparatus enabling calculation of three-dimensional coordinates of a tracking target object moving in an irradiation target of therapeutic radiation in radiation therapy from two-dimensional information about the tracking target object on fluoroscopic X-ray images captured at various angles.

BACKGROUND

Radiation therapy, in which an affected area of a patient suffering from cancer or the like is irradiated with radiation such as X-rays or charged particles, is known. Recently, for this therapy, attempts have been made to accurately recognize information about the position of the affected area and tissues around the area, by acquiring anatomical information in the patient's body immediately before the therapy, so that the therapy can be implemented while being limited to the affected area. The anatomical information in the patient's body immediately before the therapy is acquired by using a cone beam CT (CBCT) imaging device. The apparatus captures CBCT images using a fluoroscopic X-ray imaging device installed on a rotatable gantry provided to the radiation therapy apparatus for irradiating the affected area with radiation from various angles. The CBCT imaging devices intermittently capture fluoroscopic X-ray images while the gantry is rotating around the patient in a surrounding manner. The fluoroscopic X-ray images thus acquired are three-dimensionally reconstructed so that a three-dimensional image is generated. The acquired CBCT image is compared with a patient's CT image at the time of therapy planning, and thus is used for determining whether positions of the affected area as well as bones and organs around the area match the positions of those at the time of the therapy planning and for positioning the patient to make the positions match. For a patient suffering from cancer or the like, in most cases the affected area means a tumor to be treated.

In the case of radiation therapy on the patient's trunk, the tumor to be treated may move due to breathing. In such a case, irradiating the entire moving range of the tumor with radiation is conceivable; however, this involves a larger radiation dose on normal tissues. In order to focus the radiation on the tumor while reducing, as much as possible, the radiation dose on normal tissues, the following method has been performed. Specifically, a position is measured on a captured fluoroscopic X-ray image of the tracking target object (metallic marker) embedded close to the tumor in advance. The position of the tumor that is difficult to visually recognize on the fluoroscopic X-ray image is estimated from the position of the tracking target object. Then, the tumor is irradiated with radiation only when the tracking target object is at a predetermined breathing phase position. Thus, the radiation irradiation on the normal tissues is reduced. As general characteristics of the human respiratory phase, the expiratory phase is the phase with the least movement and a long duration in a single respiratory cycle. Thus, the radiation therapy described above also employs a method of emitting radiation while the respiratory state is in this expiratory phase. Therefore, for a therapy plan CT used for drafting a radiation therapy plan, an image captured in the expiratory phase state of a patient achieved by breath holding and the like is employed.

In the case of the CBCT captured immediately before the above-mentioned therapy, if a tumor is present in the trunk of the body, breathing causes movement of the tumor as well as surrounding bones and organs, resulting in blurring in the CBCT image to be acquired. When the blurring occurs in the image, the exact location of a moving tumor or organ cannot be identified, and thus the image cannot be compared with the therapy plan CT. A solution has been provided for such a problem. Specifically, the respiratory phase is determined by tracking the body surface movement of the patient using an infrared marker or by monitoring a movement of the diaphragm inside the body on the fluoroscopic X-ray images at the time of CBCT imaging. Then, only the fluoroscopic X-ray images captured in the respiratory phase that are the same as that at the time of therapy planning are used for three-dimensional reconstruction, to thereby acquire a CBCT image whose quality of which is less affected by motion blur. An imaging technique for acquiring such a CBCT image is known as a four-dimensional CBCT (4D-CBCT) imaging technique and has recently been under development. However, it has been reported that variation may arise in the correlation between the movement of the body surface and the diaphragm described above, and the movement of the tumor. Furthermore, in the case of using the diaphragm, the diaphragm may fail to appear on the fluoroscopic X-ray image at the CBCT imaging, depending on the imaging site. Furthermore, in order to accurately recognize the respiratory phase state that is the same as that at the time of patient's therapy planning, three-dimensional tracking of the movement is preferably performed directly on the tumor or is preferably performed on the tracking target object near the tumor. In recent years, as described in Patent Document 1, there has been developed a technique of measuring the three-dimensional position of a tumor with a CBCT imaging device including a fluoroscopic X-ray imaging device with two orthogonal axes during CBCT imaging, by three-dimensionally tracking the tracking target object embedded in the body to be close to the tumor.

CITATION LIST

Patent Literature

Patent Document 1: JP 2015-29793 A

SUMMARY

Technical Problem

In order to acquire three-dimensional position information about a tracking target object during CBCT imaging, an orthogonal two-axis fluoroscopic X-ray imaging apparatus needs to be installed on a gantry of a radiation therapy apparatus. Unfortunately, depending on a radiation therapy apparatus, reduction in the size and weight of the apparatus or limitation of the size of a room where it is introduced might make it difficult to achieve the apparatus configuration with two fluoroscopic X-ray imaging devices installed on the gantry. Moreover, in radiation therapy apparatuses available on market, generally, only a single fluoroscopic X-ray imaging device is installed on the gantry, while being turned by 90 degrees with respect to the irradiation direction of therapeutic X-rays and charged particles. Thus, major renovation is required to additionally install one fluoroscopic X-ray imaging device. Thus, there is a need for a technology enabling three-dimensional tracking of a tracking target object during CBCT imaging using only one fluoroscopic X-ray imaging device installed on a gantry of a radiation therapy apparatus. Generally, a single fluoroscopic X-ray imaging installed on a gantry is only capable of acquiring two-dimensional information about a tracking target object projected on an image.

Solution to Problem

The present invention relates to a radiation therapy apparatus comprising: a couch that supports an irradiation target; a gantry that is movable around the irradiation target to irradiate the irradiation target on the couch with therapeutic radiation from various angles; a fluoroscopic X-ray generation device and an X-ray flat panel detector that are installed on the gantry and used for acquiring a fluoroscopic X-ray image; a CBCT imaging device that performs cone beam CT imaging by using the fluoroscopic X-ray generation device and the X-ray flat panel detector to acquire a cone beam CT image; and a two-dimensional moving object tracking device that two-dimensionally tracks a tracking target object projected within the irradiation target in the fluoroscopic X-ray image, wherein three-dimensional coordinates of the tracking target object are obtained as coordinates that are included in a movement area set in advance, the three-dimensional coordinates being on a tracking target object passing straight line formed by connecting to each other three-dimensional coordinates in a therapy room coordinate system for an image of the tracking target object projected on each fluoroscopic X-ray image and three-dimensional coordinates of the X-ray generation device.

Preferably, the three-dimensional coordinates of the tracking target object are obtained as a midpoint between two intersecting points of the movement area of the tracking target object set in advance and the tracking target object passing straight line formed by connecting to each other the three-dimensional coordinates in the therapy room coordinate system for the image of the tracking target object projected on each fluoroscopic X-ray image and the three-dimensional coordinates of the X-ray generation device.

The present invention further relates to a radiation therapy apparatus comprising: a couch that supports an irradiation target; a gantry that is movable around the irradiation target to irradiate the irradiation target on the couch with therapeutic radiation from various angles; a fluoroscopic X-ray generation device and an X-ray flat panel detector that are installed on the gantry and used for acquiring a fluoroscopic X-ray image; a CBCT imaging device that performs cone beam CT imaging by using the fluoroscopic X-ray generation device and the X-ray flat panel detector to acquire a cone beam CT image; and a two-dimensional moving object tracking device that two-dimensionally tracks a tracking target object projected within the irradiation target in the fluoroscopic X-ray image, wherein a position of each tracking target object on a four-dimensional CT image including a position of the tracking target object in each respiratory phase acquired in advance is transferred into the therapy room coordinate system; each intersecting point or common perpendicular line between or of an inter-phase movement straight line and the tracking target object passing straight line is calculated, the inter-phase movement straight line being obtained by connecting positions of the tracking target object on the four-dimensional CT image in respiratory phases; the intersecting point is obtained as the three-dimensional coordinates of the tracking target object when the intersecting point exists; and a point on the common perpendicular line on the inter-phase movement straight line where the common perpendicular line has a shortest length is obtained as the three-dimensional coordinates of the tracking target object when the intersecting point does not exist.

The present invention further relates to a radiation therapy apparatus comprising: a couch that supports an irradiation target; a gantry that is movable around the irradiation target to irradiate the irradiation target on the couch with therapeutic radiation from various angles; a fluoroscopic X-ray generation device and an X-ray flat panel detector that are installed on the gantry and used for acquiring a fluoroscopic X-ray image; a CBCT imaging device that performs cone beam CT imaging by using the fluoroscopic X-ray generation device and the X-ray flat panel detector to acquire a cone beam CT image; a two-dimensional moving object tracking device that two-dimensionally tracks a tracking target object projected within the irradiation target in the fluoroscopic X-ray image; and a three-dimensional moving object tracking device that includes two pairs of moving object tracking X-ray generation devices and a moving object tracking X-ray flat panel detector, and that three dimensionally tracks the tracking target object on a fluoroscopic X-ray image acquired, wherein three-dimensional coordinates of the tracking target are obtained as a point on a tracking target object passing straight line formed by connecting to each other three-dimensional coordinates in a therapy room coordinate system for an image of the tracking target object projected on a fluoroscopic X-ray image acquired during the cone beam CT imaging and three-dimensional coordinates of the X-ray generation device, the point being any one of (i) a point on a three-dimensional movement trajectory of the tracking target in the therapy room coordinate system acquired from the three-dimensional moving object tracking device, (ii) a point on the three-dimensional movement trajectory where a calculated common perpendicular line, at which the three-dimensional movement trajectory and the tracking target object passing straight line perpendicularly intersect, has a shortest length, (iii) a point on the tracking target object passing straight line where a calculated common perpendicular line, at which the three-dimensional movement trajectory and the tracking target object passing straight line perpendicularly intersect, has the shortest length, and (iv) a midpoint on a length of the common perpendicular line.

Preferably, the respiratory phase of the irradiation target is determined based on the three-dimensional coordinates of the tracking target object obtained for fluoroscopic X-ray images, and the fluoroscopic X-ray images in one respiratory phase are selected, and a three-dimensional image of the irradiation target is reconstructed from the fluoroscopic X-ray image in the respiratory phase.

Advantageous Effects of Invention

According to the present invention, in conventional CBCT imaging using one fluoroscopic X-ray imaging device, position recognition with higher accuracy can be achieved for a tracking target object moving due to breathing by the human body and the like as compared with conventional cases. Thus, highly accurate three-dimensional tracking can be achieved during CBCT imaging and a high-quality four-dimensional CBCT image can be acquired.

DESCRIPTION OF EMBODIMENTS

Hereinafter, embodiments of a radiation therapy apparatus of the present invention will be described with reference to the drawings.

First Embodiment

Hereinafter, a first embodiment (Embodiment 1) of the present invention will be described with reference to FIGS. 1 to 6. The present invention can be applied to radiation therapy apparatuses such as X-ray therapy apparatuses and proton therapy apparatuses. In the first embodiment, an X-ray therapy apparatus using X-rays as therapeutic radiation will be described as an example.

Figure 1:
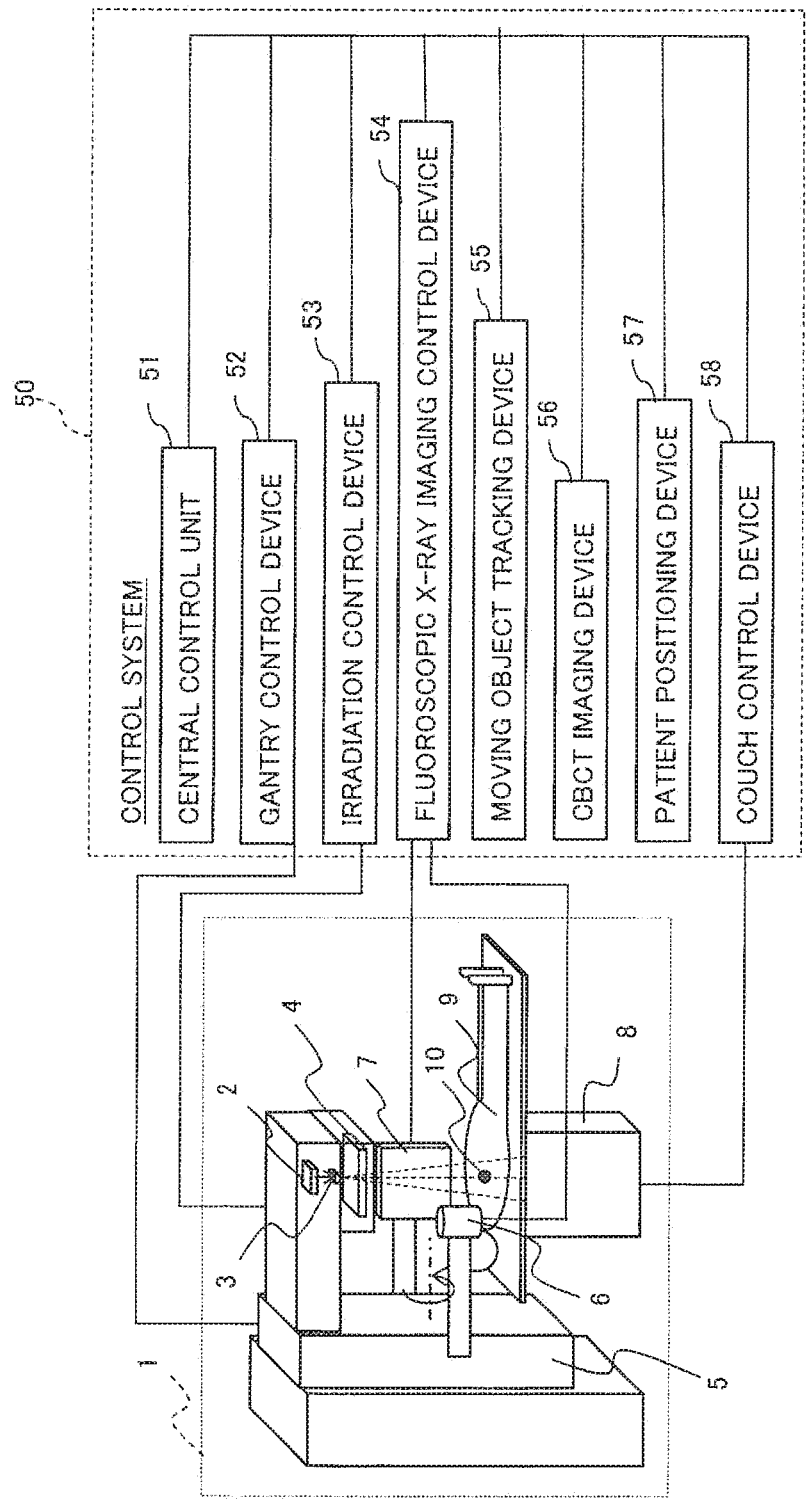
FIG. 1 is a diagram illustrating a configuration of a radiation therapy apparatus according to a first embodiment.

FIG. 1 is a diagram illustrating a schematic configuration of a radiation therapy apparatus 1 according to the embodiment. The radiation therapy apparatus 1 includes a linear accelerator 2, a heavy metal target 3, a collimator 4, a gantry 5, a fluoroscopic X-ray generation device 6, a fluoroscopic X-ray flat panel detector 7, and a couch 8.

The radiation therapy apparatus 1 accelerates electrons, generated by an electron beam generation device (not shown), with the linear accelerator 2 and causes the electrons to collide with the heavy metal target 3 to generate therapeutic radiation (X-ray). The therapeutic radiation thus generated is shaped by the collimator 4 into a shape suitable for a tumor of a patient under therapy. The linear accelerator 2, the heavy metal target 3, and the collimator 4 are attached to the gantry 5. Thus, when the gantry 5 rotates around an irradiation target 9, the linear accelerator 2, the heavy metal target 3, and the collimator 4 attached thereto also rotate around the irradiation target 9 of the therapeutic radiation. Thus, an irradiation direction to the irradiation target 9 from the collimator 4 can be controlled. A tracking target object 10 in the irradiation target 9, on the couch 8, is irradiated with the therapeutic radiation, with the angle set to be suitable for the irradiation using the gantry 5. In the case of treating a patient suffering from cancer or the like, the irradiation target 9 supported by the couch 8 is the patient, and the tracking target object 10 is a target such as a tumor or a marker. The couch 8 can move axially in an area around the center of the gantry 5 and can control the three-dimensional position of the irradiation target 9. Specifically, the three-dimensional position of the irradiation target 9 can be adjusted with the couch 8, and the irradiation direction of the therapeutic radiation can be adjusted with the gantry 5.

Furthermore, the fluoroscopic X-ray generation device 6 and the fluoroscopic X-ray flat panel detector 7 are provided on respective sides of the irradiation target 9, so that the irradiation target 9 is sandwiched by these. Therefore, X-rays from the fluoroscopic X-ray generation device 6 pass through the irradiation target 9 and are detected by the fluoroscopic X-ray flat panel detector 7, whereby a fluoroscopic image is obtained. The fluoroscopic X-ray generation device 6 and the fluoroscopic X-ray flat panel detector 7 are attached to the gantry 5 so that the X-ray transmission direction for the irradiation target 9 can be changed as the gantry 5 rotates, and thus can obtain the fluoroscopic images at a position in a vertical direction of the irradiation target 9, set by the couch 8, while rotating in a circumference direction. A straight line connecting the fluoroscopic X-ray generation device 6 and the fluoroscopic X-ray flat panel detector 7 to each other is inclined by 90 degrees relative to the irradiation direction of the therapeutic radiation.

Figure 2:
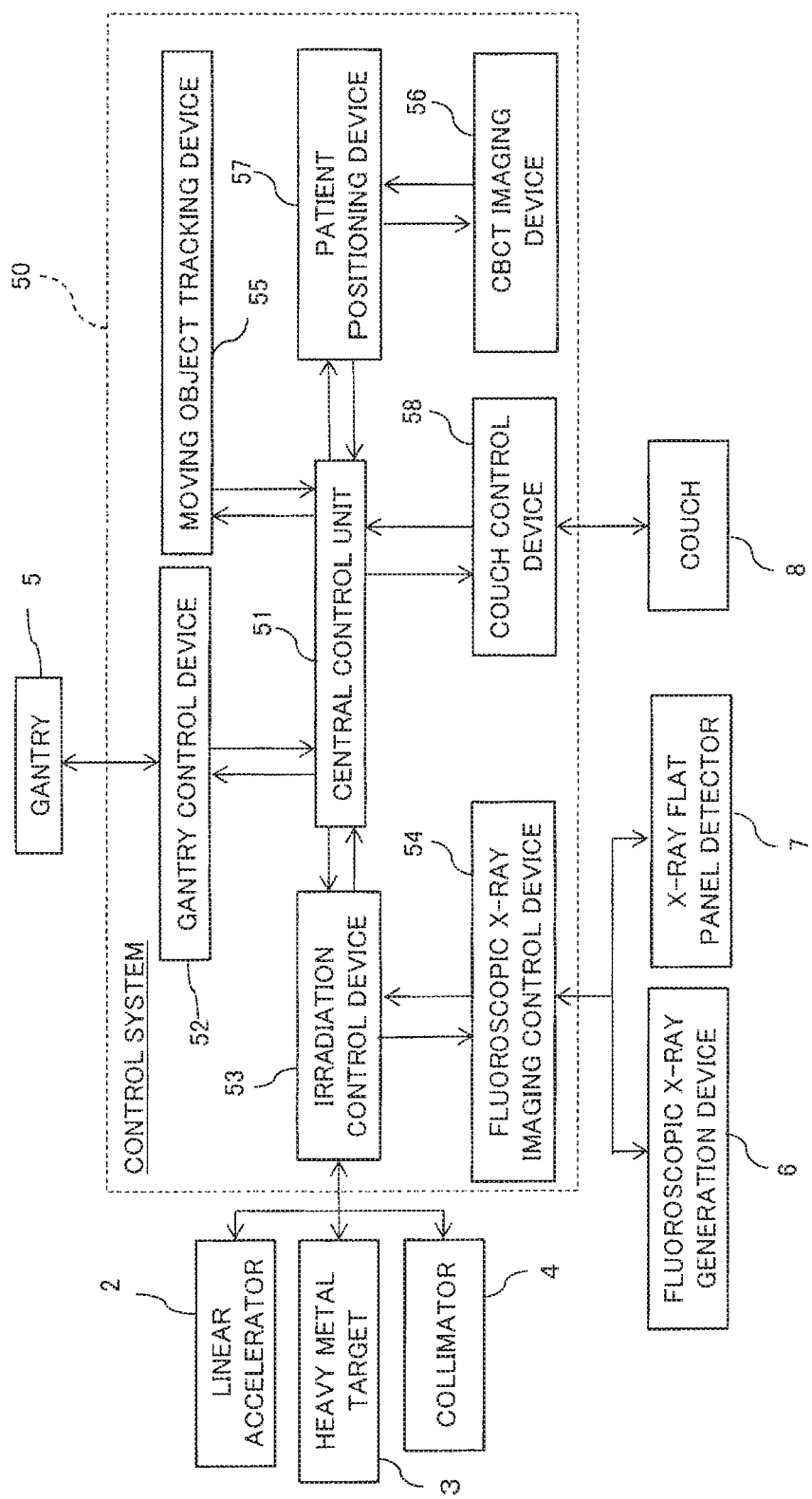
FIG. 2 is a diagram illustrating a configuration of a control system according to the first embodiment.

A control system 50 provided in the radiation therapy system of the present embodiment will be described with reference to FIG. 2. FIG. 2 illustrates control blocks of the control system 50.

The control system 50 includes a central control unit 51, a gantry control device 52, an irradiation control device 53, a fluoroscopic X-ray imaging control device 54, a moving object tracking device 55, a CBCT imaging device 56, a patient positioning device 57, and a couch control device 58.

The central control unit 51 is connected to the gantry control device 52, the irradiation control device 53, the fluoroscopic X-ray imaging control device 54, the moving object tracking device 55, the CBCT imaging device 56, the patient positioning device 57, and the couch control device 58, exchanges necessary information with these components, and controls each device of the control system 50.

The gantry control device 52 is connected to the gantry 5 and controls the gantry 5 to be at a desired angle. The irradiation control device 53 is connected to the linear accelerator 2, the heavy metal target 3, and the collimator 4 and controls these to issue a permission to shape the radiation and emit the therapeutic radiation as desired.

The fluoroscopic X-ray imaging control device 54 is connected to the fluoroscopic X-ray generation device 6 and the fluoroscopic X-ray flat panel detector 7, and controls these to intermittently perform fluoroscopic X-ray imaging, so that fluoroscopic X-ray images are acquired.

The moving object tracking device 55 can control the fluoroscopic X-ray imaging control device 54 via the central control unit 51 to acquire fluoroscopic X-ray images, and can use the acquired fluoroscopic X-ray image to recognize the position of the tracking target object 10 in the irradiation target 9. Thus, the tracking target object 10 can be tracked on the fluoroscopic X-ray images acquired intermittently. Thus, the moving object tracking device 55 serves as a two-dimensional moving object tracking device. The tracking target object 10 described herein represents a metal marker embedded in the vicinity of a tumor or represents the tumor itself.

The CBCT imaging device 56 performs CBCT imaging by performing fluoroscopic X-ray imaging while causing the gantry to rotate by controlling the gantry control device 52 and the fluoroscopic X-ray imaging control device 54 via the central control unit 51, acquires CBCT fluoroscopic X-ray images (cone beam CT images) intermittently, and three-dimensionally reconstructs the images to generate a CBCT image.

The patient positioning device 57 uses a therapy plan CT image obtained in advance and the CBCT image generated by the CBCT imaging device 56 to calculate the movement amount necessary for the patient position to match the patient position according to the therapy plan CT. The couch control device 58 is connected to the couch 8 and obtains the result of the movement amount calculation by the patient positioning device 57 via the central control unit 51, and controls the couch 8 to be suitable for the patient condition at the time of therapy planning.

Flow of Patient Positioning

Figure 3:
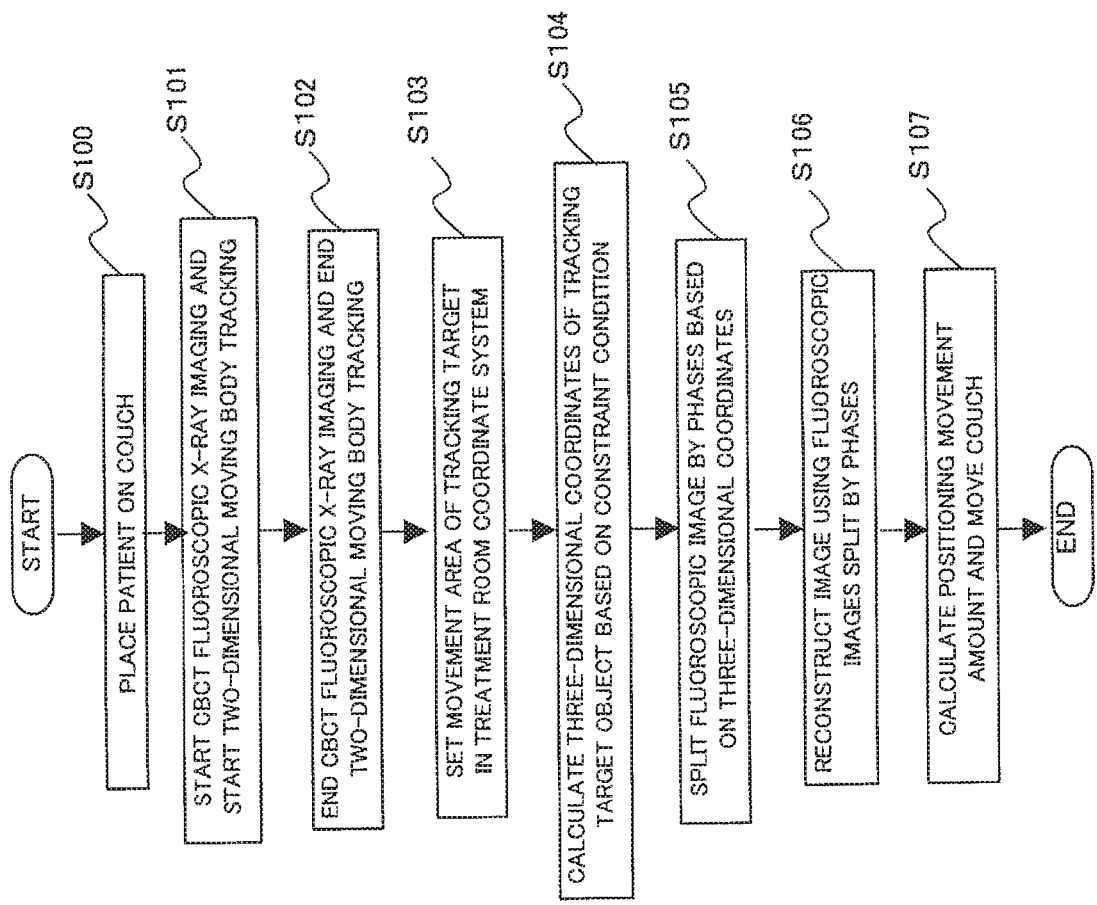
FIG. 3 is a diagram illustrating a flow of patient positioning according to the first embodiment.

A flow of patient positioning using the radiation therapy apparatus according to the present embodiment will be described with reference to FIG. 3. First of all, a patient (irradiation target 9) is placed on the couch 8 (step S100). Subsequently, the CBCT imaging device 56 starts CBCT fluoroscopic X-ray imaging by controlling the gantry control device 52 and the fluoroscopic X-ray imaging control device 54. The fluoroscopic X-ray imaging control device 54 transmits CBCT fluoroscopic X-ray images acquired at various gantry angles to the moving object tracking device 55 and the CBCT imaging device 56. Furthermore, the moving object tracking device 55 sequentially calculates the coordinates of the projection image (the tracking target object projection image 11) on the image of the tracking target object 10 projected on the CBCT fluoroscopic X-ray image, to two-dimensionally track the tracking target object 10 (step S101).

When the CBCT fluoroscopic X-ray imaging is completed, the CBCT imaging device 56 creates a three-dimensional reconstructed image (three-dimensional image) using CBCT fluoroscopic X-ray images acquired at various gantry angles. Meanwhile, the moving object tracking device 55 ends the two-dimensional tracking of the tracking target object 10 on the CBCT fluoroscopic X-ray image, and transfers the two-dimensional tracking result to the CBCT imaging device 56 (step S102).

Next, the CBCT imaging device 56 sets a movement area 12 of the tracking target object 10 on the created three-dimensional reconstructed image (step S103). For example, the movement area 12 is set as follows. Specifically, when the tracking target object 10 is a metal marker, the movement area 12 is set by manually or automatically extracting a three-dimensional area of movement of the tracking target object 10 based on the shape of the metal artifact or a marker trajectory on the reconstructed image.

Next, the three-dimensional coordinates of the tracking target object are calculated from the movement area 12 and a constraint condition (step S104). Now, the calculation of the three-dimensional coordinates will be described with reference to FIG. 4 and FIG. 5.

Figure 4:
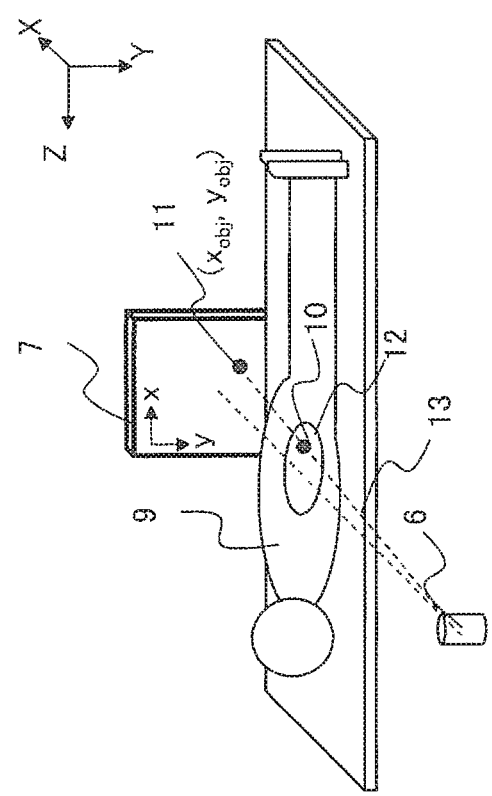
FIG. 4 is a diagram illustrating a method of setting a movement area according to the first embodiment.

In the CBCT fluoroscopic X-ray image acquired at each rotation angle of the gantry 5, the CBCT imaging device 56 converts two-dimensional coordinates $(x_{obj}, y_{obj})$, of the tracking target object projection image 11 on the image shown in FIG. 4, in a two-dimensional coordinate system (x,y), into coordinates in a three-dimensional therapy room coordinate system (X,Y,Z). Specifically, since the position of the fluoroscopic X-ray flat panel detector 7 in the therapy room coordinate system is known, based on this position, the two-dimensional coordinates of the tracking target object projection image 11 on the image in the fluoroscopic X-ray flat panel detector 7 are converted into three-dimensional coordinates in the therapy room coordinate system (X,Y,Z).

Figure 5:
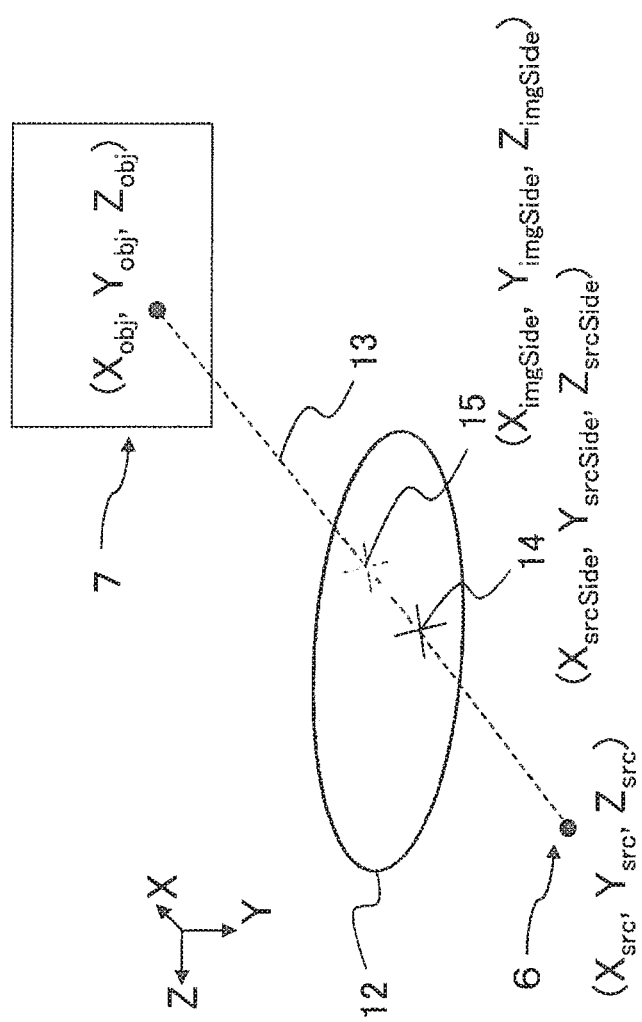
FIG. 5 is a diagram illustrating a method of calculating three-dimensional coordinates of a tracking target object using the movement area setting and constraint conditions according to the first embodiment.

Then, as illustrated in FIG. 5, a straight line between three-dimensional coordinates $(X_{obj}, Y_{obj}, Z_{obj})$ of the tracking target object projection image 11 as a result of the conversion, and coordinates $(X_{src}, Y_{src}, Z_{src})$ in the three-dimensional therapy room coordinate system of the fluoroscopic X-ray generation device 6 is calculated. Since the tracking target object 10 is present along the straight line, this straight line is referred to as a tracking target object passing straight line 13. By defining the constraint conditions that are on the tracking target object passing straight line 13 and are included in the movement area 12, a presence area of the tracking target object 10 in the therapy room coordinate system is limited.

For example, an existing position of the tracking target object 10 in the existing area thus limited is calculated as follows. Specifically, for example, as illustrated in FIG. 5, three-dimensional coordinates of the tracking target object 10 can be obtained as coordinates of a midpoint $((X_{srcSide}+X_{imgSide})/2, (Y_{srcSide}+Y_{imgSide})2, (Z_{srcSide}+Z_{imgSide})/2)$ between two points where the tracking target object passing straight line 13 and the movement area 12 intersect that are a fluoroscopic X-ray generation device side intersecting point 14 $(X_{srcSide}, Y_{srcSide}, Z_{srcSide})$ and a fluoroscopic X-ray flat panel detector side intersecting point 15 $(X_{imgSide}, Y_{imgSide}, Z_{imgSide})$.

Through a series of processes on the CBCT fluoroscopic X-ray image acquired at each gantry angle, three-dimensional coordinates of the tracking target object 10 at the time of acquiring the CBCT fluoroscopic X-ray image are calculated (step S104).

Figure 6:
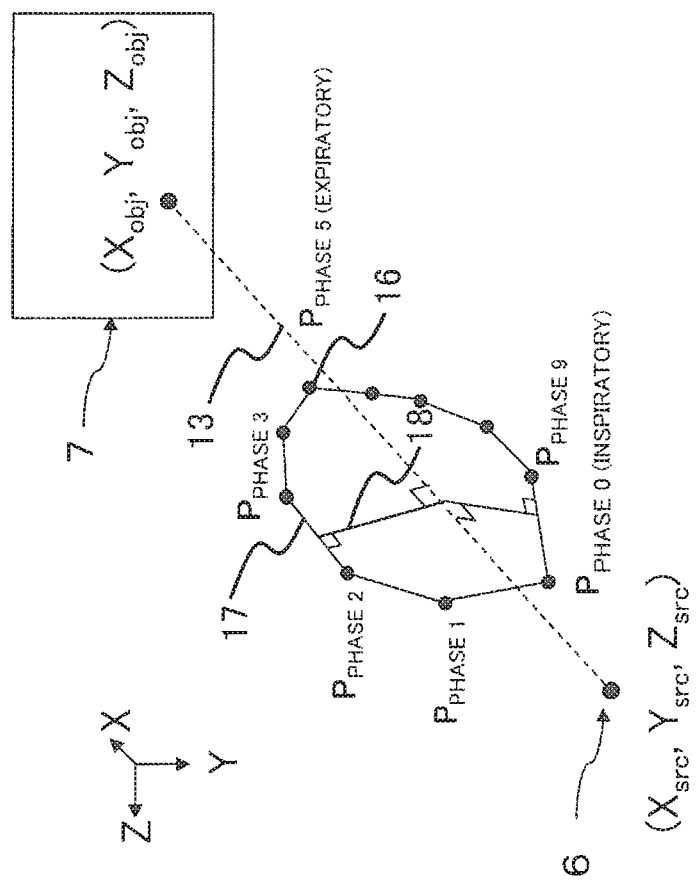
FIG. 6 is a diagram illustrating a method of calculating three-dimensional coordinates of a tracking target object using 4DCT image information according to the first embodiment.

Next, from information about the three-dimensional coordinate information of the tracking target object 10 in each CBCT fluoroscopic X-ray image acquired in step S104, the tracking target object 10 is phase-divided for each respiratory phase (step S105). Specifically, since the three-dimensional coordinates of the tracking target object 10 are obtained for each of the CBCT fluoroscopic X-ray images acquired at each rotation angle, the trajectory of the tracking target object 10 during image capturing can be obtained. From the trajectory of the tracking target object 10, the respiratory phase can be determined, and the respiratory phase can be determined for each CBCT fluoroscopic X-ray image. For example, the trajectory of the tracking target object 10 during a single breath is formed as a trajectory as illustrated in FIG. 6. Thus, the phase division can be performed according to the position of the tracking target object 10 on each CBCT fluoroscopic X-ray image.

Then, it is determined whether or not an image is in the respiratory phase (for example, expiratory phase) determined in advance at the time of therapy planning, and only the CBCT fluoroscopic X-ray image captured in the expiratory phase is selected. The reconstruction process is performed again using only the selected CBCT fluoroscopic X-ray images in the predetermined respiratory phase (step S106). In this manner, CBCT images in the same phase as the respiratory phase (e.g., expiratory phase) defined at the time of therapy planning are generated.

The CBCT image generated in step S106 is transmitted to the patient positioning device 57, and the patient positioning device 57 performs calculation processing using the received CBCT image and a therapy plan CT image to obtain an amount of movement required for the two images to match. The movement amount calculated in this manner is transmitted to the couch control device 58 via the central control unit 51, and the couch control device 58 controls the couch 8 so that a movement by the movement amount is performed (step S107). As a result, the patient (irradiation target 9) is positioned at a position where a CBCT image that matches the therapy plan CT image can be obtained.

Thus, patient positioning is completed. After the patient positioning is completed, radiation therapy based on the therapy plan starts.

Effect

According to the present embodiment, the three-dimensional position of the tracking target object 10 in the irradiation target 9 in the therapy room coordinate system can be acquired during CBCT fluoroscopic X-ray imaging. With use of the three-dimensional position information about the tracking target object 10, CBCT fluoroscopic X-ray images can selected with the respiratory phase determined. Thus, it is possible to improve the selection accuracy of the respiratory phase as compared with a conventional method where the reconstruction is performed based on the movement of the abdomen and the movement of the diaphragm. Thus, a more accurate CBCT image closer to the therapy plan CT image can be generated to contribute to an improvement of patient positioning accuracy.

Modification

The present invention is not limited to the above embodiments, and includes various modifications. The above embodiment is described in detail in order to explain the present invention in an easily understandable manner, and is not necessarily limited to modes including all the described configurations. Further, part of the configuration of one embodiment can be replaced with the configuration of another embodiment, and the configuration of another embodiment can be added to the configuration of one embodiment. In addition, it is also possible to add, delete, and replace other configurations for part of the configuration of each embodiment.

For example, in the present embodiment, and example is described where the therapeutic radiation is X-rays. However, the embodiment can be similarly applied to an apparatus using charged particles such as a proton beam or a carbon line.

Furthermore, the method of setting the movement area 12 is not limited to the method of calculating the midpoint between the two points, and the movement area 12 can be calculated and set manually or automatically from information about the therapy plan CT image. In addition, when a four-dimensional CT image (4DCT image) is acquired in advance at the time of therapy planning, the three-dimensional coordinates can be calculated with part of the processing in steps S103 and S104 omitted by using the method described with reference to FIG. 6. In the 4DCT imaging technique, as described above, the respiratory phase is determined by monitoring the movement of the body surface of the patient and the movement of the diaphragm.

In FIG. 6, a P phase 0 (inspiratory) corresponds to coordinates as a result of transferring, into the three-dimensional therapy room coordinate system, the tracking target position on the CT image at the time of a phase 0 (inspiratory) in the 4DCT image with a point. For example, the transferring of the coordinates is implemented as follows. Specifically, fluoroscopic X-ray images of the front and side of the patient are acquired before the CBCT imaging, and three-dimensional coordinates of the expiratory phase of the tracking target object in the therapy room coordinate system are acquired. Then, the conversion is performed so that the coordinates match the tracking target object three-dimensional coordinates on an CT image corresponding to a phase 5 (expiration) of the 4DCT image. As a result, the three-dimensional coordinates on CT images of other phases are transferred into a therapy room coordinate system as relative coordinates relative to the expiratory phase.

Next, a line connecting the coordinates of the tracking target object between the phases can be generated as an inter-phase movement straight line 17 represented by $L_{phase2\text{-}3}$. This means that nine inter-phase movement straight lines 17 can be generated in the therapy room coordinate system when there 4DCT images of 10 phases. If there is a point (intersection point) between any of the nine phase-to-phase movement straight lines 17 (step S104) and the tracking target object passing straight line 13 similarly obtained, the three-dimensional coordinates of the intersecting point in the therapy room coordinate system may be the three-dimensional coordinates to be obtained. If the intersecting point does not exist, three-dimensional coordinates are calculated with the following method.

A straight line $CL_{phase2\text{-}3}$ perpendicularly intersecting with the tracking target object passing straight line 13 and the inter-phase movement straight line 17 is generated as a phase common perpendicular line 18. The phase common perpendicular line 18 is generated for each of the inter-phase movement straight lines 17. Thus, when there are nine inter-phase movement straight lines 17, nine phase common perpendicular lines 18 are generated. Next, the length (common perpendicular length) of the created phase common perpendicular line 18 is calculated, and the coordinates of the midpoint of the shortest phase common perpendicular line 18 are calculated as three-dimensional coordinates of the tracking target object.

Note that it is also preferable to prioritize the presence of the tracking target object 10 on the tracking target object passing straight line 13, and thus the intersecting point between the tracking target object passing straight line 13 and the phase common perpendicular line 18 at the position with the shortest phase common perpendicular line 18 (a point on the tracking target object passing straight line with the shortest common perpendicular line) may be obtained as the three-dimensional coordinates of the tracking target object 10.

With this method described above, the tracking target object three-dimensional coordinates in the therapy room coordinate system can be calculated more accurately.

Second Embodiment

Hereinafter, a second embodiment (Embodiment 2) of the present invention will be described with reference to FIGS.

7 to 10. The second embodiment is applied to a radiation therapy apparatus obtained by adding a moving object tracking fluoroscopic X-ray imaging control device, capable of three-dimensionally calculating the position where the tracking target object 10 is present in the irradiation target 9, to the radiation therapy apparatus such as an X-ray therapy apparatus or a proton therapy apparatus described in Embodiment 1. The three-dimensional position of the tracking target object 10 on the fluoroscopic image acquired in the CBCT imaging is calculated by using three-dimensional movement information about the tracking target object 10 on the fluoroscopic image acquired by intermittently capturing images of the irradiation target 9 using the moving object tracking fluoroscopic X-ray imaging control device immediately before patient positioning in the radiation therapy apparatus.

Figure 7:
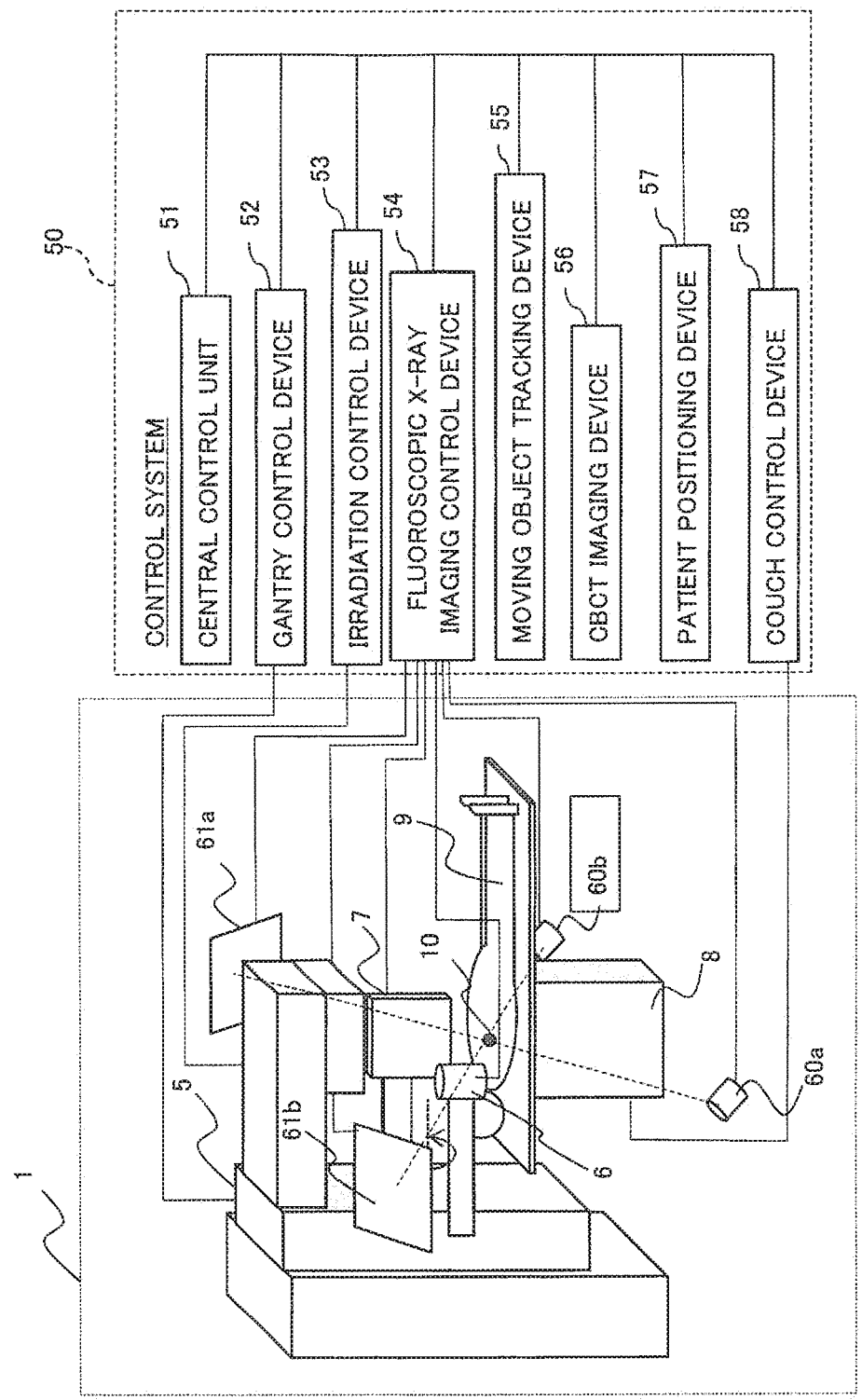
FIG. 7 is a diagram illustrating a configuration of a radiation therapy apparatus according to a second embodiment.
Figure 8:
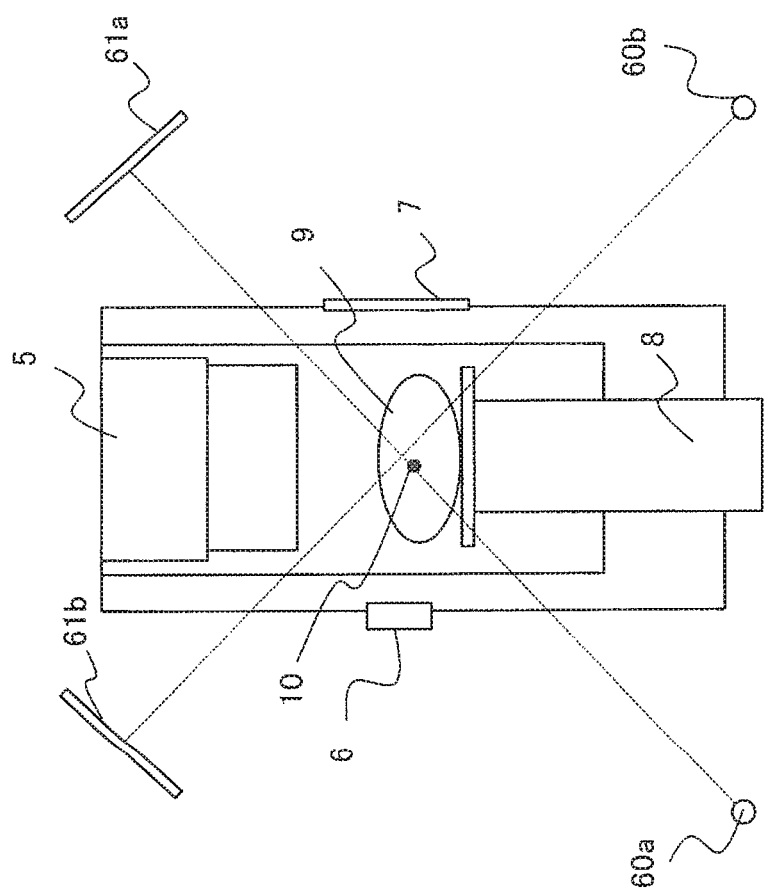
FIG. 8 is a diagram illustrating a side surface of the configuration of the radiation therapy apparatus according to the second embodiment.

In the present embodiment, as in the first embodiment, the X-ray therapy apparatus will be described as an example. First of all, as illustrated in FIG. 7, the moving object tracking fluoroscopic X-ray imaging control device is a device including two pairs of moving object tracking X-ray generation devices 60 and moving object tracking X-ray flat panel detectors 61, the former and the latter being respectively provided under the floor and on the ceiling of a room (therapy room) where the radiation therapy apparatus 1 illustrated in FIG. 1 is installed. These two pairs of devices intermittently capture fluoroscopic X-ray images and the three-dimensional position of the tracking target object 10 is calculated on the images acquired, whereby the tracking target object 10 is tracked over time. FIG. 8 is a side view of the radiation therapy apparatus 1 illustrated in FIG. 7, enabling easy understanding of the arrangement of the device configurations thereof Although the illustration is partially omitted in FIG. 7 so as not to be redundant with respect to the illustration in FIG. 1, it is assumed that the device configuration includes all the component devices illustrated in FIG. 1.

The description of the control system 50 provided in the radiation therapy system of the present embodiment is similar to the above description with reference to FIG. 2 referred to in the description of Embodiment 1. Still, there is a difference that two pairs of moving object tracking X-ray generation devices 60a and 60b and moving object tracking X-ray flat panel detectors 61a and 61b are added to the devices connected to the fluoroscopic X-ray imaging control device 54 in Embodiment 1. The fluoroscopic X-ray imaging control device 54 acquires fluoroscopic X-ray images from each of the two moving object tracking X-ray flat panel detectors 61 by intermittently performing fluoroscopic X-ray imaging by controlling the two pairs of devices. The moving object tracking device 55 reads the two fluoroscopic X-ray images, obtains the two-dimensional coordinates of the tracking target object 10 on each of the fluoroscopic X-ray images intermittently captured, and executes calculation processing on the coordinates in accordance with the gantry angle to calculate the three-dimensional coordinates of the tracking target object 10 on the therapy room coordinate system over time. Thus, the moving object tracking device 55 according to this embodiment operates not only as a two-dimensional moving object tracking device but also as a three-dimensional moving object tracking device that performs three-dimensional tracking of the tracking target object 10. Control for other device configurations is as described in the embodiment.

Flow of Patient Positioning

Figure 9:
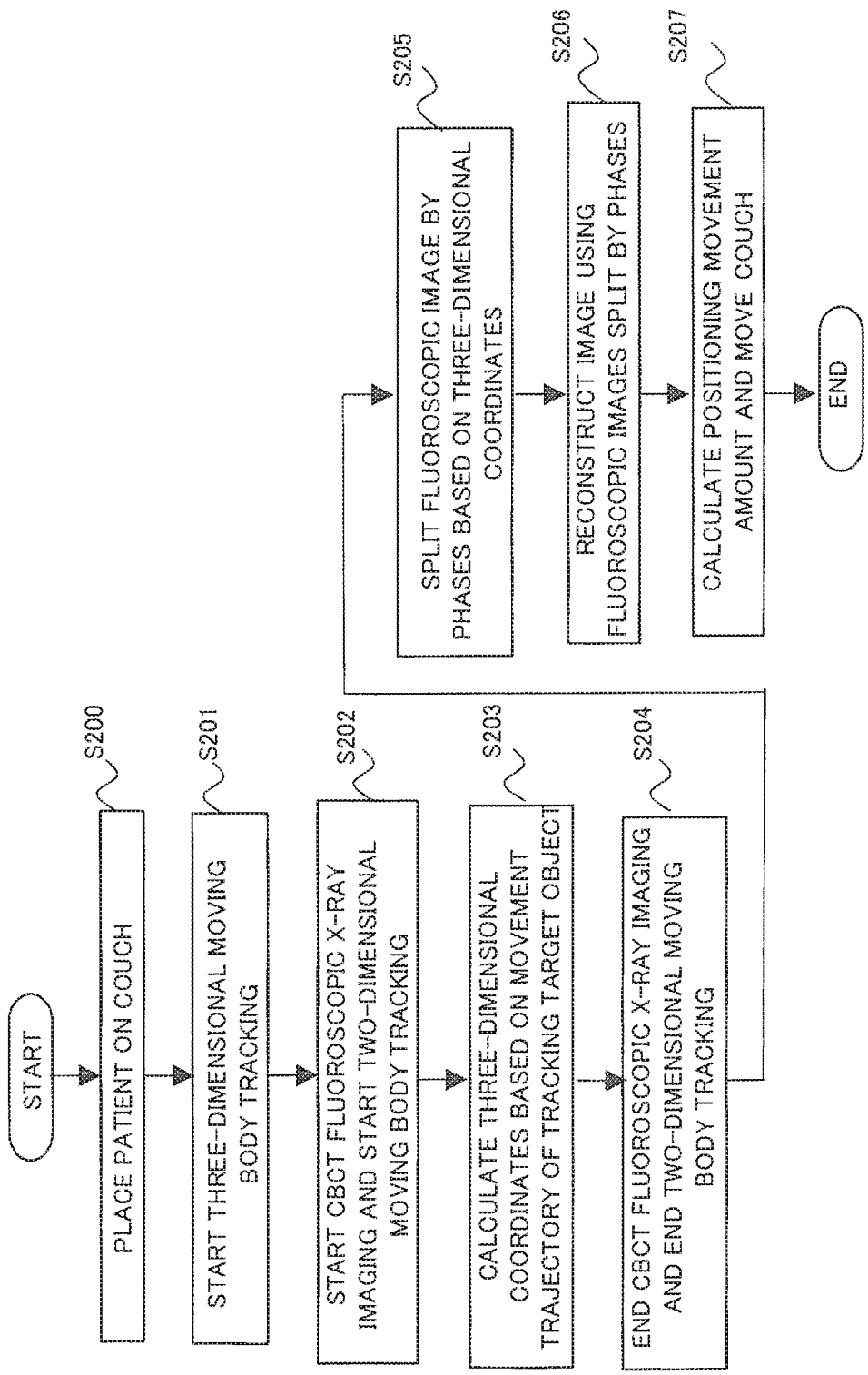
FIG. 9 is a diagram illustrating a flow of patient positioning according to the second embodiment.

A flow of patient positioning using the radiation therapy apparatus according to the present embodiment will be described with reference to FIG. 9. First of all, the irradiation target 9 (patient) is placed on the couch 8 (step S200).

Next, the moving object tracking device 55 controls the fluoroscopic X-ray imaging control device to intermittently capture fluoroscopic X-ray images for ten and several seconds to several tens of seconds with the two pairs of moving object tracking X-ray generation devices 60a and 60b and the moving object tracking X-ray flat panel detectors 61a and 61b. Then, the three-dimensional coordinates of the tracking target object 10 in the therapy room coordinate system are calculated from the two fluoroscopic X-ray images acquired. The obtained three-dimensional coordinates are connected over time to be stored in the moving object tracking device 55 as information about a tracking target object movement trajectory 62 (step S201).

Subsequently, the CBCT imaging device 56 starts CBCT fluoroscopic X-ray imaging by controlling the gantry control device 52 and the fluoroscopic X-ray imaging control device 54 (step S202). The fluoroscopic X-ray imaging control device 54 transmits CBCT fluoroscopic X-ray images acquired at various gantry angles to the moving object tracking device 55 and the CBCT imaging device 56. The moving object tracking device 55 two-dimensionally tracks the tracking target object 10 by calculating the coordinates on the images of the tracking target object 10 projected on the CBCT fluoroscopic X-ray images.

Figure 10:
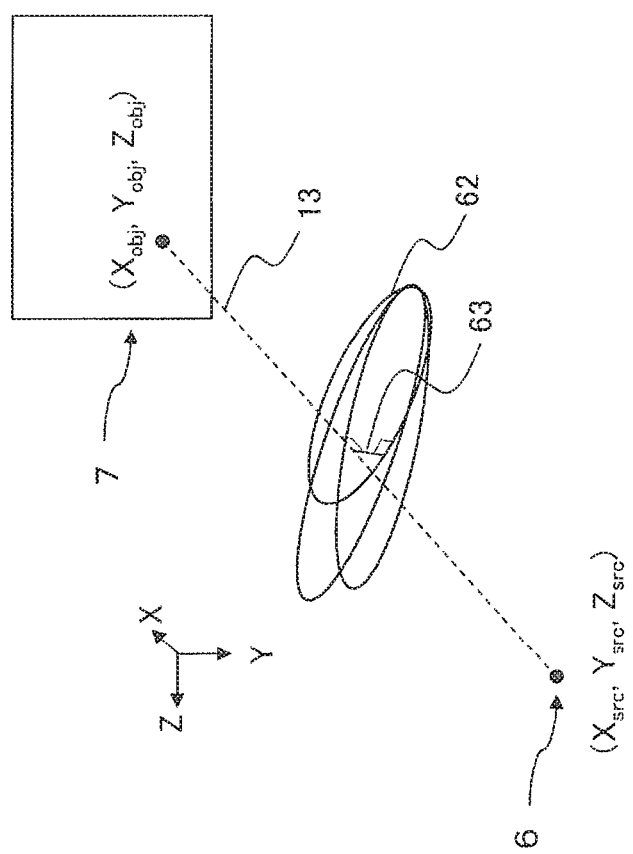
FIG. 10 is a diagram illustrating a method of calculating three-dimensional coordinates of a tracking target object according to the second embodiment.

Next, the CBCT imaging device 56 calls the information about the tracking target object movement trajectory 62 stored in the moving object tracking device 55, and calculates the three-dimensional coordinates of the tracking target object from the information about the tracking target object movement trajectory 62 and the two-dimensional information about the tracking target object 10 obtained in step S201. As shown in FIG. 10, when there is a point (intersecting point) where the tracking target object movement trajectory 62 intersects with the tracking target object passing straight line 13 defined in Embodiment 1, the intersecting point is obtained as three-dimensional coordinates of the tracking target object 10. If there is no such intersecting point, a trajectory common perpendicular line 63 perpendicularly intersecting with the tracking target object movement trajectory 62 and the tracking target object passing straight line 13 is generated. Then, the tracking target object movement trajectory 62 is searched for a position with the shortest trajectory common perpendicular line 63. The three-dimensional coordinates of the midpoint of the trajectory common perpendicular line 63 at the position with the shortest trajectory common perpendicular line 63 may be obtained as the three-dimensional coordinates of the tracking target object 10 to be obtained (step S203).

Note that it is also preferable to prioritize the presence of the tracking target object 10 on the tracking target object passing straight line 13, and thus the intersecting point between the tracking target object passing straight line and the trajectory common perpendicular line 63 at the position with the shortest trajectory common perpendicular line 63 (a point on the tracking target object passing straight line with the shortest common perpendicular line) may obtained as the three-dimensional coordinates of the tracking target object 10.

When all the CBCT fluoroscopic X-ray imaging is completed, the CBCT imaging device 56 stores the acquired fluoroscopic X-ray images in the CBCT imaging device 56 (step S204).

Next, the CBCT imaging device 56 determines, from the three-dimensional coordinate information acquired in step S203, whether or not the tracking target object 10 is in the respiratory phase determined in advance at the time of therapy planning, and only the CBCT fluoroscopic X-ray image captured in the respiratory phase is selected (step S205).

By performing the reconstruction process again by only using the CBCT fluoroscopic X-ray images selected in step S205, a CBCT image in the same phase as the respiratory phase determined at the therapy planning time point is generated (step S206). The CBCT image generated in step S206 is transmitted to the patient positioning device 57, and the patient positioning device 57 executes calculation processing using the received CBCT image and the therapy plan CT image to obtain an amount of movement required for the two images to match. The calculated movement amount is transmitted to the couch control device 58 via the central control unit 51, and the couch control device 58 controls the couch 8 to move by the movement amount (step S207). When the above flow ends, patient positioning is completed. When the patient positioning is completed, radiation therapy starts.

Effect

With the present embodiment, the three-dimensional position, in the therapy room coordinate system, of the tracking target object 10 in the irradiation target 9 can be acquired during the CBCT fluoroscopic X-ray imaging, based on the three-dimensional movement trajectory information about the tracking target object 10 obtained immediately before the CBCT imaging. Thereby, the three-dimensional position information can be calculated more accurately than in the method described in the first embodiment. As a result, the respiratory phase is determined from the movement of the abdomen and the movement of the diaphragm, which is the conventional method, and the CBCT fluoroscopic X-ray image is selected and the selection accuracy of the respiratory phase is improved as compared to the case where the respiratory phase is reconstructed. Since an accurate CBCT image can be created and used closer to the therapy plan CT image, it can contribute to the improvement of patient positioning accuracy.

Modification

The present invention is not limited to the above embodiment, but includes various modifications. The above embodiment is described in detail in order to explain the present invention in an easily understandable manner, and is not necessarily limited to modes including all the described configurations. Further, part of the configuration of one embodiment can be replaced with the configuration of another embodiment, and the configuration of another embodiment can be added to the configuration of one embodiment. In addition, it is also possible to add, delete, and replace other configurations for part of the configuration of each embodiment.

For example, in the present embodiment, and example is described where the therapeutic radiation is X-rays. However, the embodiment can be similarly applied to an apparatus using charged particles such as a proton beam or a carbon line. The two pairs of moving object tracking X-ray generation devices 60 and moving object tracking X-ray flat panel detectors 61 can be arranged either under the floor or on the ceiling. In order to prevent overlapping between a moving object tracking fluorescent X-ray imaging range and the structure of the gantry 5 depending on the rotation angle of the gantry 5, two or more pairs of the devices can be arranged under the floor and on the ceiling, or the devices may be moved in a device room so that the arrangement of the two pairs of the devices changes in accordance with a situation. Furthermore, it is also possible to install the two pairs of devices on the gantry 5. However, in this case, it is assumed that CBCT image can only be captured by one pair of imaging devices.

Experimental Example

Figure 11:
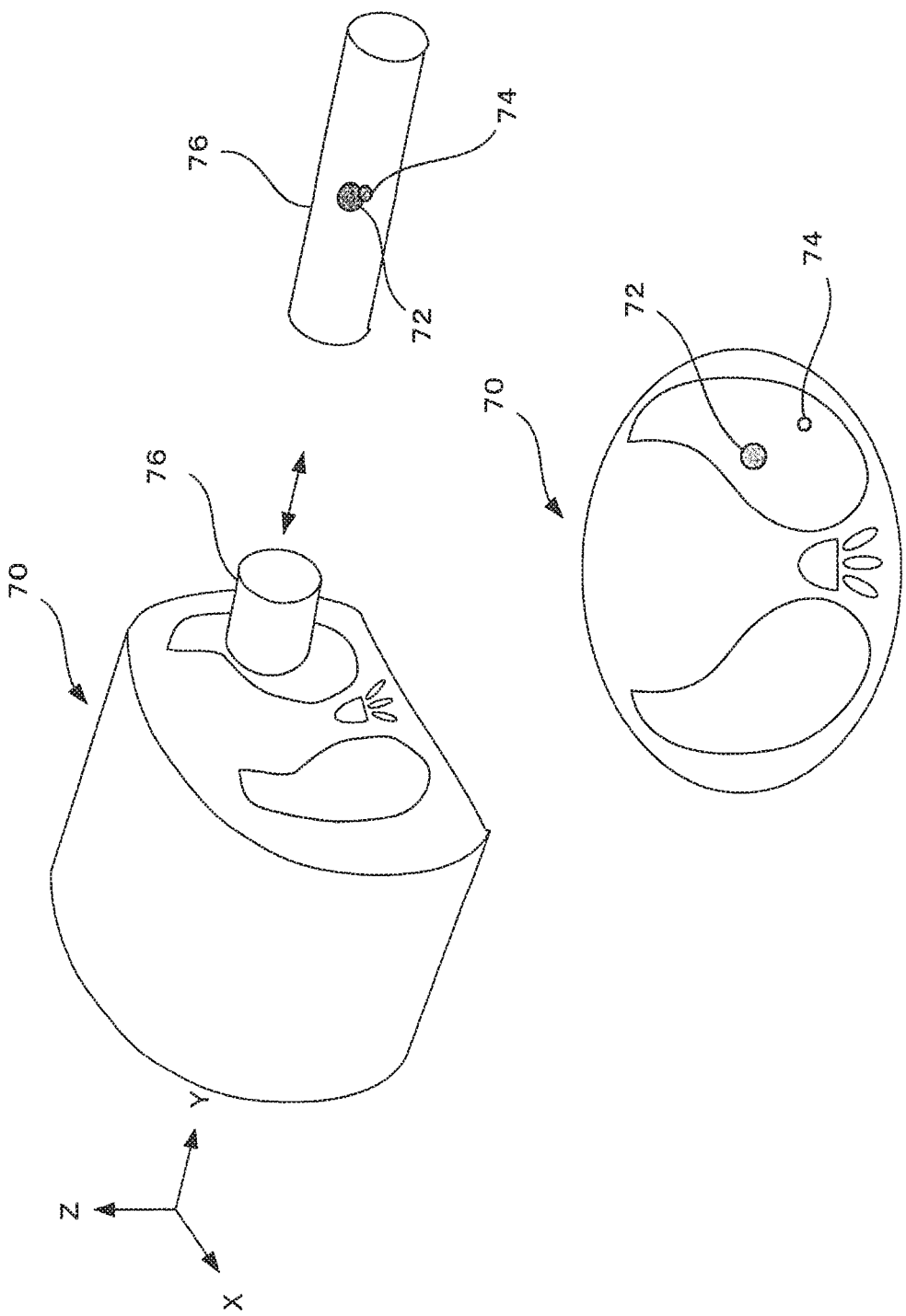
FIG. 11 is a view illustrating a part of an experimental apparatus.

An experiment was conducted using a movable thorax phantom 70 illustrated in FIG. 11. The movable thorax phantom 70 has a part provided with a hole elongated in a craniocaudal direction (Y direction), and an insertion rod 76 in which a tumor model 72 and a gold marker 74 are embedded was movably inserted in the hole. The insertion rod 76 can be reciprocated in a Z direction by an actuator (not shown). Therefore, the tumor model 72 and the gold marker 74 reciprocate in the Y direction with respect to the movable thorax phantom 70. The tumor model 72 and the gold marker 74 three-dimensionally move with the movable thorax phantom 70 and the actuator further moving two-dimensionally in the lateral direction (X direction) and a ventrodorsal direction (Z direction).

Such a movable thorax phantom 70 was placed on the couch 8 of the radiation therapy apparatus 1 shown in FIG. 1, and the tumor model 72 and the gold marker 74 were moved three dimensionally. Then, the movable thorax phantom 70 was irradiated with X-rays from the fluoroscopic X-ray generation device 6, and the two-dimensional position of the gold marker 74 was detected by the fluoroscopic X-ray flat panel detector 7. Then, the three-dimensional position of the gold marker 74 was identified by the method described in the second embodiment described above (the intersecting point between the trajectory common perpendicular line and the tracking target object passing straight line was obtained as the three-dimensional coordinates of the tracking target object (gold marker 74)).

Here, the diameter of the tumor model 72 was 10 mm, and the diameter of the gold marker 74 was 2 mm. All of the movement waveforms in the X, Y, and Z directions were $\cos^4\theta$, a cycle was four seconds, and amplitudes were Y: ±10 mm, X: ±5 mm, and Z: ±1.5 mm.

Figure 12:
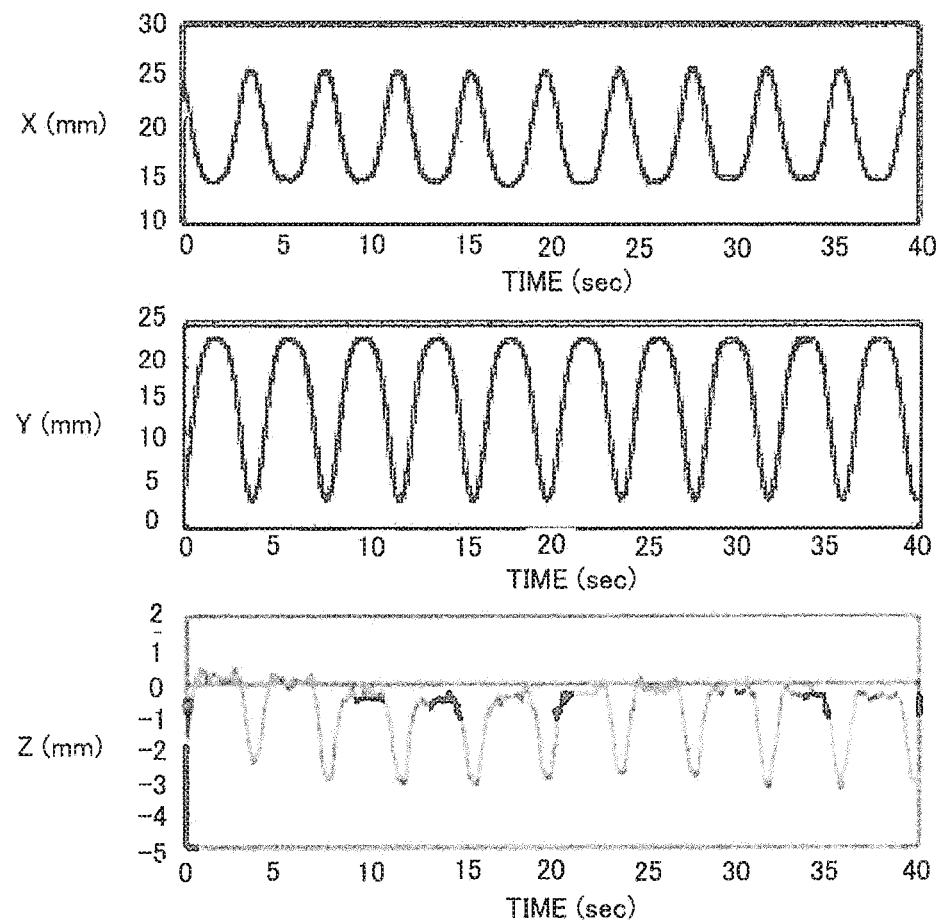
FIG. 12 is a diagram illustrating a change in a tracking target object position, estimated by the system of the embodiment, over time.
Figure 13:
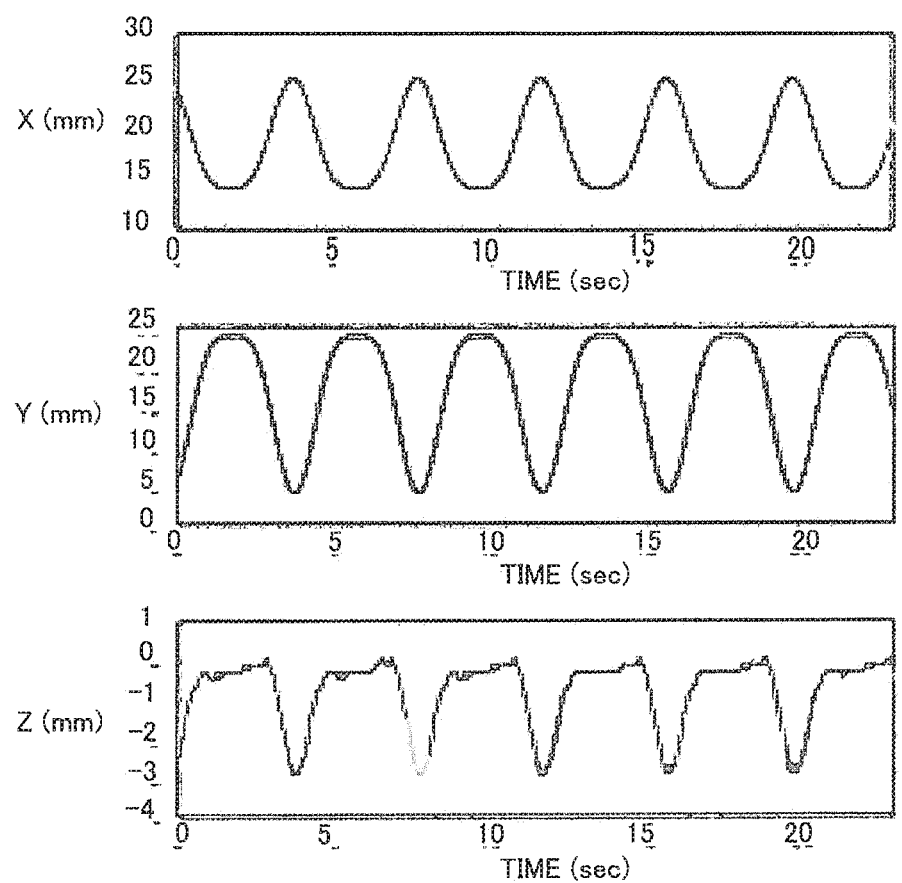
FIG. 13 is a diagram illustrating an actual change in the tracking target object position over time.
Figure 14:
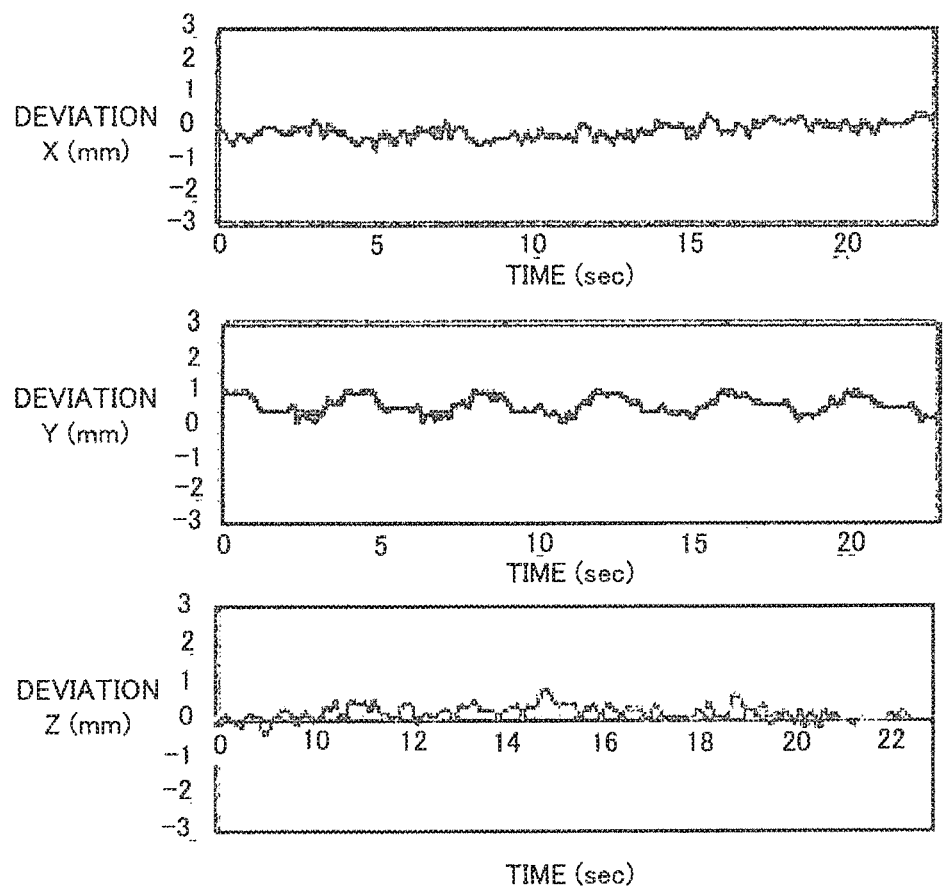
FIG. 14 is a view illustrating a change in deviation of the estimated tracking target object position over time.

FIG. 12 illustrates a change in three-dimensional coordinates of the gold marker 74, estimated by the above method, over time. Furthermore, FIG. 13 illustrates a change in the position of the gold marker 74 over time, based on the actual movement information. FIG. 14 illustrates the difference between the estimated value in FIG. 12 and the actual position in FIG. 13. It can be seen that the deviation of the estimated position of the gold marker 74 according to the present embodiment illustrated in FIG. 12 from the actual position was small (not larger than 1 mm), proving that the method according to the present embodiment can implement highly accurate position detection.

Figure 15:
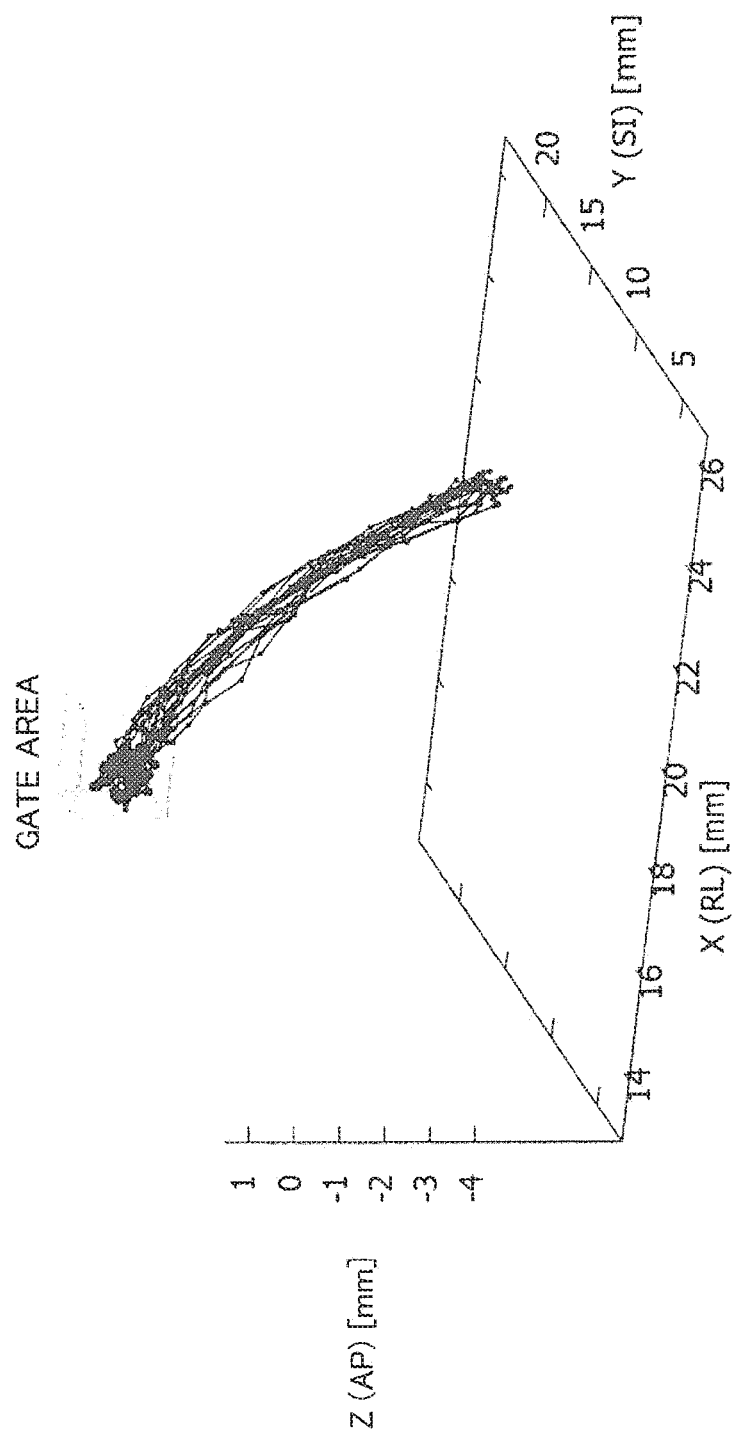
FIG. 15 is a diagram illustrating a position of a gate area.

FIG. 15 illustrates a change in the position of the detected tracking target object over time. A rectangular parallelepiped box represents a gate area in which the irradiation of the therapeutic radiation is performed. With the position detected, the therapeutic radiation is emitted when the tumor enters the gate area, so that the tumor can be irradiated with the therapeutic radiation, whereby radiation therapy can be appropriately performed.

REFERENCE SIGNS LIST

1 Radiation therapy apparatus
2 Linear accelerator
3 Heavy metal target
4 Collimator
5 Gantry
6 Fluoroscopic X-ray generation device
7 Fluoroscopic X-ray flat panel detector 8 Couch
9 Irradiation target
10 Tracking target object
11 Tracking target object projection image
12 Movement area
13 Tracking target object passing straight line
14 Fluoroscopic X-ray generation device side intersecting point
15 Fluoroscopic X-ray flat panel detector side intersecting point
16 Point P phase 5 (expiration) where tracking target object coordinates on 4DCT image are transferred into therapy room coordinate system
17 Inter-phase movement straight line $L_{phase2\text{-}3}$
18 Phase common perpendicular line $CL_{phase2\text{-}3}$
50 Control system
51 Central control unit
52 Gantry control device
53 Irradiation control device
53
54 Fluoroscopic X-ray imaging control device
55 Moving object tracking device
56 CBCT imaging device
57 Patient positioning device
58 Couch control device
60a, 60b Moving object tracking X-ray generation device
61a, 61b Moving object tracking X-ray flat panel detector
62 Tracking target object movement trajectory
63 Trajectory common perpendicular line

The invention claimed is:

1. A radiation therapy apparatus comprising:
a couch that supports an irradiation target;
a gantry that is movable around the irradiation target to irradiate the irradiation target on the couch with therapeutic radiation from various angles;
a fluoroscopic X-ray generation device and an X-ray flat-panel detector that are installed on the gantry and configured to acquire a fluoroscopic X-ray image; and
a control system comprising:
   a CBCT imaging device;
   a moving-object tracking device; and
   a central control unit configured to control:
      the CBCT imaging device to control the fluoroscopic X-ray generation device and the X-ray flat-panel detector to acquire a cone-beam CT image; and
      the moving-object tracking device to two-dimensionally track a tracking target object projected within the irradiation target in the fluoroscopic X-ray image,
wherein the CBCT imaging device calculates three-dimensional coordinates of the tracking target object as a midpoint between two intersecting points between a movement area of the tracking target object set in advance and the tracking target object passing a straight line formed by connecting to each other three-dimensional coordinates in a therapy room coordinate system for an image of the tracking target object projected on each fluoroscopic X-ray image and three-dimensional coordinates of the fluoroscopic X-ray generation device.

2. The radiation therapy apparatus according to claim 1, wherein
the CBCT imaging device determines a respiratory phase of the irradiation target based on the three-dimensional coordinates of the tracking target object obtained for fluoroscopic X-ray images, and reconstructs a three-dimensional image of the irradiation target from a selected one or more of the fluoroscopic X-ray images in the respiratory phase.

3. A radiation therapy apparatus comprising:
a couch that supports an irradiation target;
a gantry that is movable around the irradiation target to irradiate the irradiation target on the couch with therapeutic radiation from various angles;
a fluoroscopic X-ray generation device and an X-ray flat-panel detector that are installed on the gantry and used for acquiring a fluoroscopic X-ray image; and
a control system comprising:
   a CBCT imaging device;
   a moving-object tracking device; and
   a central control unit configured to control:
      the CBCT imaging device to perform cone-beam CT imaging by using the fluoroscopic X-ray generation device and the X-ray flat-panel detector to acquire a cone-beam CT image; and
      the moving-object tracking device to two-dimensionally track a tracking target object projected within the irradiation target in the fluoroscopic X-ray image, wherein
the moving-object tracking device transfers a position of each tracking target object on a four-dimensional CT image including a position of the tracking target object in each respiratory phase acquired in advance into a therapy room coordinate system, the CBCT imaging device calculates each intersecting point or a common perpendicular line between or of an inter-phase movement straight line and a tracking target object passing straight line, the CBCT imaging device obtains the inter-phase movement straight line by connecting positions of the tracking target object on the four-dimensional CT image in respiratory phases, the CBCT imaging device obtains an intersecting point as three-dimensional coordinates of the tracking target object when the intersecting point exists, and a point on the common perpendicular line on the inter-phase movement straight line, where the CBCT imaging device obtains the common perpendicular line, which has a shortest length, as the three-dimensional coordinates of the tracking target object when the intersecting point does not exist.

4. The radiation therapy apparatus according to claim 3, wherein
the CBCT imaging device determines a respiratory phase of the irradiation target based on the three-dimensional coordinates of the tracking target object obtained for fluoroscopic X-ray images, and reconstructs a three-dimensional image of the irradiation target from a selected one or more of the fluoroscopic X-ray images in the respiratory phase.

5. A radiation therapy apparatus comprising:
a couch that supports an irradiation target;
a gantry that is movable around the irradiation target to irradiate the irradiation target on the couch with therapeutic radiation from various angles;
a fluoroscopic X-ray generation device and an X-ray flat-panel detector that are installed on the gantry and used for acquiring a fluoroscopic X-ray image; and
a control system comprising:
   a CBCT imaging device;
   a moving-object tracking device; and
   a central control unit configured to control:
      the CBCT imaging device to perform cone-beam CT imaging by using the fluoroscopic X-ray generation device and the X-ray flat-panel detector to acquire a cone-beam CT image; and the moving-object tracking device to two-dimensionally track a tracking target object projected within the irradiation target in the fluoroscopic X-ray image, wherein the moving-object tracking device obtains three-dimensional coordinates of the tracking target object as coordinates that are included in a movement area set in advance, the three-dimensional coordinates being on a tracking target object passing straight line formed by connecting to each other three-dimensional coordinates in a therapy room coordinate system for an image of the tracking target object projected on each fluoroscopic X-ray image and three-dimensional coordinates of the fluoroscopic X-ray generation device, and the CBCT imaging device determines a respiratory phase of the irradiation target based on the three- dimensional coordinates of the tracking target object obtained for fluoroscopic X-ray images, and reconstructs a three-dimensional image of the irradiation target from a selected one or more of the fluoroscopic X-ray images in the respiratory phase.

6. A radiation therapy apparatus comprising:
a couch that supports an irradiation target;
a gantry that is movable around the irradiation target to irradiate the irradiation target on the couch with therapeutic radiation from various angles;
a fluoroscopic X-ray generation device and an X-ray flat-panel detector that are installed on the gantry and used for acquiring a fluoroscopic X-ray image;
a pair of moving-object tracking X-ray generation devices;
a pair of moving-object tracking X-ray flat-panel detectors; and
a control system comprising:
a CBCT imaging device;
a moving-object tracking device; and
a central control unit configured to control:
the CBCT imaging device to perform cone-beam CT imaging by using the fluoroscopic X-ray generation device and the X-ray flat-panel detector to acquire a cone-beam CT image;
the moving-object tracking device to two-dimensionally track a tracking target object projected within the irradiation target in the fluoroscopic X-ray image and to three-dimensionally track the tracking target object on a fluoroscopic X-ray image acquired with the pair of moving-object tracking X-ray generation devices and the pair of moving-object tracking X-ray flat-panel detectors, wherein the moving-object tracking device obtains three-dimensional coordinates of the tracking target object as a point on a tracking target object passing straight line formed by connecting to each other three-dimensional coordinates in a therapy room coordinate system for an image of the tracking target object projected on a fluoroscopic X-ray image acquired during the cone-beam CT imaging and three-dimensional coordinates of the fluoroscopic X-ray generation device, the point being any one of:
  (i) a point on a three-dimensional movement trajectory of the tracking target object in the therapy room coordinate system acquired from the moving-object tracking device,
  (ii) a point on a three-dimensional movement trajectory of the tracking target object in the therapy room coordinate system, where a calculated common perpendicular line, at which the three- dimensional movement trajectory and the tracking target object passing straight line perpendicularly intersect, has a shortest length,
  (iii) a point on a tracking target object passing straight line, where a calculated common perpendicular line, at which a three-dimensional movement trajectory of the tracking target object in the therapy room coordinate system and the tracking target object passing straight line perpendicularly intersect, has a shortest length, and
  (iv) a midpoint on a length of a common perpendicular line.

7. The radiation therapy apparatus according to claim 6, wherein
the CBCT imaging device determines a respiratory phase of the irradiation target based on the three-dimensional coordinates of the tracking target object obtained for fluoroscopic X-ray images, and reconstructs a three-dimensional image of the irradiation target from a selected one or more of the fluoroscopic X-ray images in the respiratory phase.

* * * * *